United States Patent [19]

Hanslik et al.

[11] Patent Number: 4,770,663
[45] Date of Patent: Sep. 13, 1988

[54] KNEE JOINT ENDOPROSTHESIS

[76] Inventors: Lothar Hanslik, Leo-Baeck-Str. 23, D-1000 Berlin 37; Joachim E. Henssge, Im Trentsaal 7, D-2400 Lübeck, both of Fed. Rep. of Germany

[21] Appl. No.: 897,783
[22] PCT Filed: Nov. 29, 1985
[86] PCT No.: PCT/DE85/00505
  § 371 Date: Jul. 23, 1986
  § 102(e) Date: Jul. 23, 1986
[87] PCT Pub. No.: WO86/03117
  PCT Pub. Date: Jun. 5, 1986

[30] Foreign Application Priority Data

Nov. 29, 1984 [DE] Fed. Rep. of Germany ....... 3444001

[51] Int. Cl.$^4$ .................................................. A61F 2/38
[52] U.S. Cl. ............................................................ 623/20
[58] Field of Search ....................................... 623/16–23

[56] References Cited

U.S. PATENT DOCUMENTS 3,748,662 7/1973 Helfet ..................................... 623/21
4,267,608 5/1981 Bora, Jr. ............................... 623/21

FOREIGN PATENT DOCUMENTS 3314038 10/1983 Fed. Rep. of Germany ........ 623/21

Primary Examiner—Richard J. Apley
Assistant Examiner—David Isabella
Attorney, Agent, or Firm—Mark P. Stone; F. Eugene Davis, IV

[57] ABSTRACT

The invention relates to knee joint endoprosthesis consisting of a femur part provided with two skid surfaces leaving a free space between each other, said surfaces being connected with each other in front and having their curvature increasing from the front towards the rear and being curved also on planes perpendicular to said curvature; a tibia part having two surfaces on which the skid surfaces ride in a sliding manner, with an elevation being disposed between said two surfaces; and of artificial connecting means for keeping the two parts of the prosthesis together. The invention lies in the fact that the outer surface (2) of the tibia part is largely plane on a center sectional plane from the front to the rear; that the inner surface (1) of the tibia part is slightly concave on a center sectional plane from the front to the rear; that the slope (6) of the elevation (3; 4) to the outer surface (2) is flatter than the slope (5) of the elevation (3; 4) to the inner surface (1); and that the parts of the prosthesis are kept together by two ending, non-flexible bands, of which a first band extends from the front center of the tibia part upwardly and on the outside and inclined rearwardly to the femur part, and of which bands a second band extends from the rear center of the tibia part upwardly and on the inside and inclined to the front to the femur part, whereby the bands are taut when the knee is stretched, and slightly relaxed in the unstressed state when the knee is bent. In said way, the motions of the prosthesis conform closer to the natural motions than heretofore.

15 Claims, 4 Drawing Sheets

KNEE JOINT ENDOPROSTHESIS

The invention relates to a knee joint endoprosthesis consisting of a femur part provided with two skid surfaces leaving between each other a free space, said surfaces being connected with each other in front and having their curvature increasing from the front towards the rear and being curved also on planes perpendicular to said curvature, and of a tibia part having two surfaces on which the skid surfaces ride in a sliding manner, with an elevation being disposed between said two surfaces, and of artificial connecting means for keeping together the two parts of the prosthesis.

In a known prosthesis of said type (DE-PS No. 25 49 819), each of the two surfaces of the tibia part is highly concave from the front to the rear on a center sectional plane, i.e., the sliding surfaces of the femur part are fitted congruently. The slopes from the elevuation to the two surfaces are the same, and the parts of the prosthesis are kept together by way of two lugs in the elevation and two grooves in the skids, said grooves being engaged by said lugs. The drawback of said joint is that the conditions of motion are very imperfectly conforming to the conditions of motion in a natural joint.

The invention is based on the problem of developing the above prosthesis in a way such that the conditions of motion are more closely conforming to the natural conditions of motion as compared to the known case, and that phenomena of wear are avoided.

According to the invention, said problem is solved in that the outer surface of the tibia part is largely plane on a center sectional plane from the front to the rear; that the inner surface of the tibia part is slightly concave on a center sectional plane from the front to the rear; that the slope of the elevation to the outer surface is flatter than the slop of the elevation to the inner surface; and that the parts of the prosthesis are kept together by two ending, non-elastic bands, of which a first band extends from the center of the front of the tibia part upwardly, on the outside and inclined rearwardly to the femur part, and of which bands a second band extends from the center in the rear of the tibia part upwardly, on the inside and inclined to the front to the femur part, whereby the bands are taunt when the knee is stretched, and slightly relaxed in the unstressed state when the knee is bent.

In said way, the following is achieved: when bending the joint, the zone of contact of the inner skid sweeps a small arc on the surface associated with it, whereas the zone of contact of the outer skid sweeps a large arc on the surface associated with it, which conforms to the natural conditions.

The following applies with respect to the tension of the bands: The bands are taut when the knee is stretched, and slightly relaxed in the unstressed state when the knee is bent. In the stressed, bent state, both bands are taunt. When the knee is bent in the unstressed state from the stretched position, the tension of the bands decreases gradually.

Of course, the points where the bands are connected with the parts of the prosthesis have to be disposed in a way such that the possible motions are not interfered with. For example, the band extending from the front bottom upwardly and on the outside may not be connected to the tibia part too far in front. Owing to the fact that the curvatures of the skids of the femur part decrease rearwardly, trouble-free bending of the joint is assured.

According to another feature of the invention, two elevations are provided between the surfaces, whereby the outer elevation is disposed slightly to the rear of the inner elevation, and said elevations are connected with each other by way of a saddle surface. In this way, the center part of the tibia part is adapted to the different positions of the bands in the different angular positions of the knee.

It is proposed, furthermore, that the slope to the outer surface gradually changes into the surface with a conical shape.

According to another feature of the invention, the inner and outer surfaces slope off rearwardly within the rear zone. In this way, in the highly bent state, the femur part is capable of sliding or rolling off on said two slopes, which facilitates the bending motion of the knee.

Finally, it is proposed that the bands are rigidly connected with the tibia part before the prosthesis is implanted in the human leg, and subsequently connected with the femur part or femur while the prosthesis is being implanted.

Additional details of the invention are disclosed in the drawing, in which.

Figure 1:
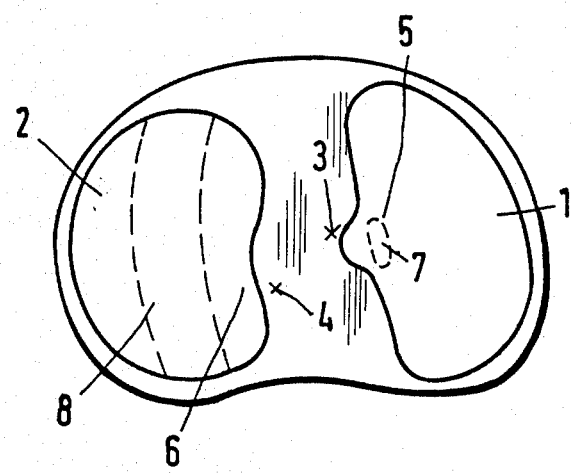
FIG. 1 is a top view of an embodiment of a tibia part of a prosthesis according to the invention.

In FIG. 1, the tibia part of the prosthesis is shown viewed from the top. Reference numeral 1 relates to the inner skid surface for the femur part of the prosthesis, and reference numeral 2 relates to the outer skid surface for the femur part of the prosthesis. Two elevations are disposed between the surfaces 1 and 2, their peaks are identified by reference numerals 3 and 4. The slope from the elevation 3 in surface 1, said slope being identified by numeral 5, is steeper than the slope 6 from the elevation 4 into the surface 2. The sliding surface 1 is slightly concave, whereas the sliding surface 2 is substantially planar. The result of said shapes is that when the knee is bent, the two skids of the femur part come into contact with the surfaces 7 and 8, which are shown shaded in FIG. 1. Thus the inner skid sweeps over a small zone 7, whereas the outer skid sweeps a large zone 8. Assuming that the tibia is stationary and the thigh is bent relative to the tibia, the thigh is performing in the course of bending a slight motion of swivel counterclockwise (related to FIG. 1). In other words, with the thigh stationary, the tibia performs in the course of bending a motion of swivel around its longitudinal axis in a way such that a front point of the tibia is slightly turned inwardly. The conditions should be such that when the knee is bent at an angle of 90 degrees, the angle of swivel of the tibia around its longitudinal axis amounts to about 20°.

Figure 2:
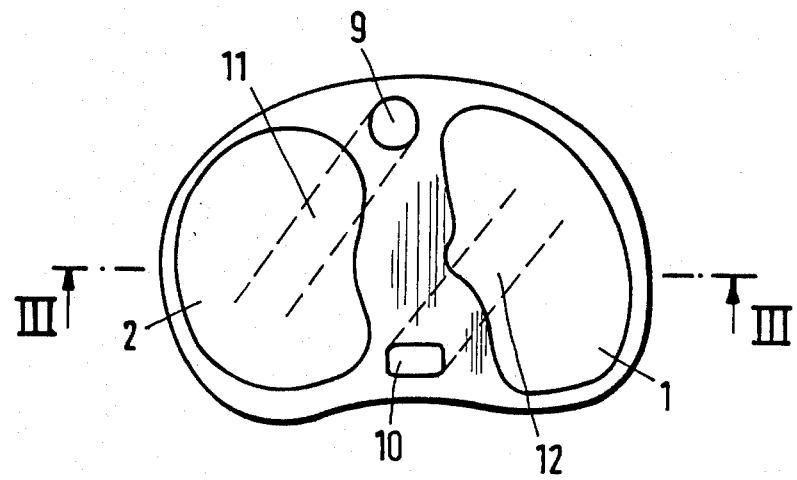
FIG. 2 is a top view of said tibia part.

FIG. 2 shows another top view of the tibia part of the prosthesis. In FIG. 2, the two bands 11 and 12 are shown. Said bands are connected with the tibia part at points 9 and 10, from where they extend upwardly (see the dash-dotted lines 11 and 12) into the femur part.

Figure 3:
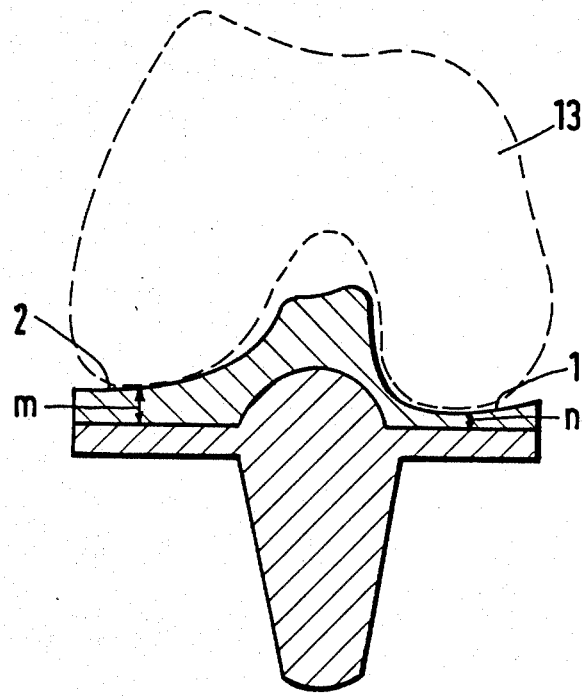
FIG. 3 shows a cut along line III—III in FIG. 2.

FIG. 3 shows a sectional view with a cut through the tibia part of the prosthesis along line III—III in FIG. 2. FIG. 3 shows that the surface 2 is disposed at a higher level than the surface 1 (spacing "m" is larger than spacing "n"). The femur part 13 is shown by the dashed line. The following applies to the front and rear:

$$1.48 < m/n < 1.52,$$

in particular: $m/n = 1.5$

The following applies to the center:

$$1.98 < m/n < 2.02,$$

in particular: $m/n = 2$.

It is thus apparent from FIG. 3 that the m/n ratio described above and shown in the drawings represents a ratio of the relative thickness of the outer tibia surface (2) relative to the inner tibia surface (1) when these surfaces are viewed in cross section.

Figure 4:
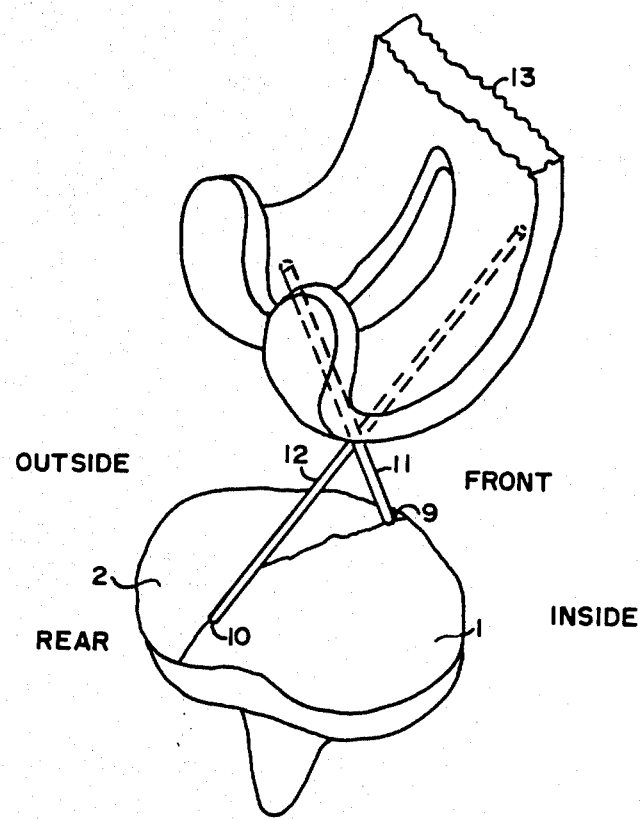
FIG. 4 shows a perspective view of the invention in which the tibia and femur parts are connected together with connection bands.

FIG. 4 illustrates a perspective view of the invention in which a first nonelastic band 11 is connected with the tibia part at the region designated by reference numeral 9, while a second nonelastic band 12 is connected with the tibia part at the region designated by reference numeral 10. The other ends of the bands 11 and 12 extend upwardly into the femur part 13. The first band 11 extends from the front center of the tibia part upwardly and to the outside of the femur part and inclined rearwardly to the femur part, while the second band 12 extends from the rear center of the tibia part upwardly and to the inside of the femur part and inclined to the front of the femur part. Reference numeral 1 illustrates the inner surface of the tibia part, and reference numeral 2 illustrates the outer surface of the tibia part, as were previously discussed.

What is claimed is:

1. A knee joint endoprosthesis having a femur part provided with two skid surfaces defining a free space therebetween, said skid surfaces being connected with each other along a front surface and being increasingly curved in a first direction from the front surface towards rear portions of said skid surfaces and being curved also on planes perpendicular to said first direction of curvature; a tibia part having inner and outer surfaces on which the skid surfaces slide, said inner and outer surfaces being joined along at least one elevated section; and artificial connecting means for securing said femur part and said tibia part together, the outer surface (2) of the tibia part being substantially planar on a center sectional plane in a direction from a front portion to a rear portion of said tibia part; the inner surface (1) of the tibia part being slightly concave on a center sectional plane from the front portion to the rear portion; the slope (6) of the elevated section (3; 4) towards the outer surface (2) being flatter than the slope (5) of the elevated surface (3; 4) towards the inner surface (1); said connecting means including two ending, non-elastic bands (11; 12), of which a first band extends from the front center of the tibia part upwardly and to the outside of the femur part and inclined rearwardly to the femur part, and of which a second band (12) extends from the rear center of the tibia part upwardly and to the inside of the femur part and inclined to the front to the femur part, said bands (11, 12) being taut when the knee is stretched, and slightly relaxed in the unstressed state when the knee is bent.

2. The knee joint endoprosthesis of claim 1, in which an inner and outer elevated section are provided between the partial tibia surfaces (1; 2), the outer elevated section (4) being disposed slightly to the rear of the inner elevated section (3), said elevated sections being connected with each other along a concave surface.

3. The knee joint endoprosthesis of claim 1, wherein the slope (6) to the outer surface (2) gradually changes into the outer surface (2) in the shape of a cone.

4. The knee joint endoprosthesis of claim 1, in which the outer surface (2) of the tibia part is more highly elevated than the inner surface (3) of the tibia part.

5. The knee joint endoprosthesis of claim 4, in which the skid surface of the femur part supported on the outer tibia surface (2) is more highly elevated than the skid surface of the femur part supported on the inner tibia surface (1).

6. The knee joint endoprosthesis of claim 1 in which the inner and outer tibia surface (1; 2) decrease in slope in a rearward direction at the rear part of said inner and outer tibia surfaces.

7. The knee joint endoprosthesis of claim 2 wherein the slope (6) to the outer surface (2) gradually changes into the outer surface (2) in the shape of a cone.

8. The knee joint endoprothesis of claim 2, in which the outer surface (2) of the tibia part is more highly elevated than the inner surface (3) of the tibia part.

9. The knee joint endoprothesis of claim 3, in which the outer surface (2) of the tibia part is more highly elevated than the inner surface (3) of the tibia part.

10. The knee joint endoprothesis of claim 8, characterized by the fact that the skid surface of the femur part supported on the outer tibia surface (2) is more highly elevated than than the skid surface of the femur part supported on the inner tibia surface (1).

11. The knee joint endoprosthesis of claim 9, characterized by the fact that the skid surface of the femur part supported on the outer tibia surface (2) is more highly elevated than than the skid surface of the femur part supported on the inner tibia surface (1).

12. The knee joint endoprosthesis of claim 2, in which the inner and outer tibia surfaces (1; 2) decrease in slope in a rearward direction at the rear part of said inner and outer tibia surfaces.

13. The knee joint endoprosthesis of claim 3, in which the inner and outer tibia surfaces (1; 2) decrease in slope in a rearward direction at the rear part of said inner and outer tibia surfaces.

14. The knee joint endoprosthesis of claim 4, in which the inner and outer tibia surfaces (1; 2) decrease in slope in a rearward direction at the rear part of said inner and outer tibia surfaces.

15. The knee joint endoprosthesis of claim 5, in which the inner and outer tibia surfaces (1; 2) decrease in slope in a rearward direction at the rear part of said inner and outer tibia surfaces.

* * * * *

UNITED STATES PATENT AND TRADEMARK OFFICE
CERTIFICATE OF CORRECTION

PATENT NO. : 4,770,663

DATED : September 13, 1988

INVENTOR(S) : Hanslik & Henssge

It is certified that error appears in the above—identified patent and that said Letters Patent is hereby corrected as shown below:

Column 3, after line 13: add the following paragraph:

-- Furthermore, it is proposed that the outer surface of the tibia part is disposed on a higher level than the inner surface of the tibia part relative to the ground or floor on which the wearer is standing. This applies analogously to the two skid surfaces of the femur part. --

Signed and Sealed this

Seventh Day of March, 1989

Attest:

DONALD J. QUIGG

Attesting Officer

Commissioner of Patents and Trademarks